United States Patent
Germaneau et al.

(10) Patent No.: US 8,772,224 B2
(45) Date of Patent: Jul. 8, 2014

(54) PERFUMING SOLUTION STABILIZED WITH RESPECT TO ULTRAVIOLET RADIATION

(75) Inventors: Sylvie Germaneau, Saint Jean de Braye (FR); Valerie Alard, Orleans (FR); Eric Perrier, Les Cotes d'Arey (FR); Maud Guyot, Chateauneuf sur Loire (FR)

(73) Assignee: LVMH Recherche, Saint Jean de Braye (FR)

( * ) Notice: Subject to any disclaimer, the term of this patent is extended or adjusted under 35 U.S.C. 154(b) by 3 days.

(21) Appl. No.: 13/554,228

(22) Filed: Jul. 20, 2012

(65) Prior Publication Data

US 2013/0045913 A1 Feb. 21, 2013

(30) Foreign Application Priority Data

Jul. 21, 2011 (FR) ...................... 11 56642

(51) Int. Cl.
*A61Q 13/00* (2006.01)
(52) U.S. Cl.
USPC ............................................................ 512/2
(58) Field of Classification Search
CPC ........... A61K 8/34; A61K 8/35; A61K 8/891; A61K 8/375; A61K 8/37; A61Q 13/00
USPC ........................................................... 512/2
See application file for complete search history.

(56) References Cited

U.S. PATENT DOCUMENTS

| 6,936,241 | B2 | 8/2005 | Yamada et al. | |
|---|---|---|---|---|
| 7,087,650 | B2 | 8/2006 | Lennon | |
| 7,214,365 | B2 * | 5/2007 | Wendel et al. | 424/59 |
| 2004/0253186 | A1 * | 12/2004 | Maillan et al. | 424/47 |
| 2008/0069898 | A1 | 3/2008 | Smith et al. | |
| 2011/0200543 | A1 | 8/2011 | Josso | |
| 2013/0046029 | A1 | 2/2013 | Germaneau et al. | |

FOREIGN PATENT DOCUMENTS

| DE | 10327468 | | 1/2005 |
|---|---|---|---|
| DE | 102005059742 | | 6/2007 |
| EP | 0717313 | | 6/1996 |
| EP | 1864648 | | 7/2007 |
| EP | 1905483 | | 4/2008 |
| EP | 2236173 | | 10/2010 |
| EP | 2324819 | | 5/2011 |
| FR | 2915387 | | 10/2008 |
| FR | 2915387 | A1 * | 10/2008 |
| FR | 2916346 | | 11/2008 |
| FR | 2916347 | | 11/2008 |
| FR | 2923385 | | 5/2009 |
| FR | 2953715 | | 6/2011 |
| WO | WO2005/042828 | | 5/2005 |
| WO | WO2006/005846 | | 1/2006 |

OTHER PUBLICATIONS

English Translation of FR2915387A1 obtained Sep. 17, 2013 at http://worldwide.espacenet.com/publicationDetails/original Document?CC=FR&NR=2915387A1&KC=A1&FT=D&ND=3& date=20081031&DB=EPODOC&Iocale=en_EP.*
Database GNPD [Online] Mintel: "Rain Water Body Mist", XP002678133, Oct. 2008, Database accession No. 993834.*

* cited by examiner

*Primary Examiner* — Ling Choi
*Assistant Examiner* — Lanee Reuther
(74) *Attorney, Agent, or Firm* — Hamre, Schumann, Mueller & Larson, P.C.

(57) ABSTRACT

The invention relates to a perfuming solution comprising a volatile alcohol, a perfume and a mixture for stabilizing said perfume consisting of at least one UV filter selected from the derivatives of cinnamate, at least one UV filter selected from the derivatives of dibenzoylmethane, and at least one non-volatile oil that is soluble in said alcohol and is a solvent for said filters, the stabilizing mixture being in sufficient amount to protect the perfuming solution from degradation by UV radiation.

14 Claims, No Drawings

PERFUMING SOLUTION STABILIZED WITH RESPECT TO ULTRAVIOLET RADIATION

The invention relates to a perfuming solution comprising a perfume stabilized by a mixture of two particular UV filters dissolved in a non-volatile oil.

PRIOR ART

Perfuming solutions are generally in the form of a fresh water, a toilet water, a perfume water, a perfume, an aftershave lotion, or a care water.

They are transparent and are packaged in bottles that are also transparent, so that these products are particularly exposed to light, to ultraviolet radiation (also called "UV radiation" or "UV" in the present application) and to temperature variations.

Now, daylight and UV radiation cause degradation of the molecules such as the perfumes and colorants that these solutions contain. In particular, the following may be observed: a change of the perfume, a decoloration, yellowing, turning pink, flocculation and precipitates of substances, or clouding, which may adversely affect the consumer's perception of the product and the efficiency of pumps, when they are packaged as sprays.

To protect perfuming solutions from such degradation throughout their useful life, generally filters that are active against UV (also called "UV filters" in the present application) and an antioxidant system are incorporated in them, in order to guarantee their stability.

It has always been stated in the prior art that the use of two UV filters will not protect a perfume from degradation by UV. Thus, ternary or quaternary mixtures of UV filters have been proposed in order to guarantee stabilization of perfumes.

For example, it was shown in application FR 2 916 346 that the colour and the odour of a toilet water comprising 1 wt. % of a mixture of n-hexyl 2-(4-diethylamino-2-hydroxybenzoyl)benzoate and ethylhexyl methoxycinnamate 35/65 are degraded on exposure to UV and heat, so that it is necessary to add a third UV filter of the butylmethoxy-dibenzoylmethane type to obtain effective protection of the product against UV.

Moreover, the colour and the odour of a toilet water comprising 1 wt. % of ethylhexylmethoxycinnamate and 0.3 wt. % of butylmethoxydibenzoylmethane are degraded on exposure to UV and heat. This is why it was proposed in application WO 2006/005846 to add a third filter, ethylhexyl salicylate, to ethylhexylmethoxycinnamate and to butylmethoxydibenzoylmethane to protect cosmetic compositions from decoloration when they are exposed to UV.

Applications FR 2 916 347 and FR 2 923 385 also describe mixtures of filters comprising a cinnamate and a dibenzoylmethane to guarantee stability of the colour and odour of a toilet water. These quaternary mixtures comprise a cinnamate, a dibenzoylmethane and a salicylate derivative, in combination with either a derivative of hydroxyaminobenzophenone, or a derivative of benzotriazole.

However, ethylhexyl salicylate has the drawback of being odorous: it releases a greasy, pyrogenous, plastic, rubber note, so that its use for stabilization of perfuming solutions is not satisfactory; depending on the percentage at which it is introduced for this application, it may lead to degradation of the authenticity of the perfume.

Finally, it has been proposed to add, to a mixture of UV filters comprising a cinnamate and a dibenzoylmethane, an organic compound comprising a nitroxyl or hydroxylamine group such as tris-tetra-methylhydroxypiperidinol (marketed under the reference Tinogard Q) for protecting fabrics, cosmetic compositions and household maintenance products from the effects of light, heat and oxidation (patent application WO 2005/042828).

Unfortunately the stabilizing additives recommended in the patent applications of the prior art contain large amounts of UV filters, which are raw materials that are expensive and tend to alter the colour or the scent of the perfuming solution.

Increasing the quantity of filters in the perfumes has also been tried, in order to protect the products against UV radiation; however, this route was not successful, because at higher concentrations the film of perfume vaporized on the skin leaves a greasy sensation and because regulatory requirements impose maximum limits to the level of use of each UV filter.

AIM OF THE INVENTION

Therefore there is still a need to propose new stabilizers of perfuming products that do not have the drawbacks of the stabilizers of the prior art, and notably stabilizing mixtures that do not alter the organoleptic properties such as odour and colour of the perfuming product, while providing sufficient stabilization of the product exposed to daylight or to temperature differences.

Stabilizers that are less expensive and do not alter the organoleptic properties such as odour and colour of perfumes and of toilet waters, while providing sufficient stabilization of the product exposed to daylight or to temperature differences, are therefore sought.

The applicant discovered, surprisingly, that this aim could be achieved by combining two particular UV filters and a non-volatile, preferably polar, oil.

Contrary to the teaching of the prior art, which suggests using at least three UV filters to obtain sufficient stabilization of perfuming solutions with respect to the action of UV, the inventors found that it is possible, against all expectations, to use only two UV filters in a toilet water while guaranteeing sufficient stability of the perfume and of the colour. It is also possible to incorporate amounts of UV filters less than those recommended in the prior art while guaranteeing sufficient stability. The inventors found, surprisingly, that certain non-volatile oils make it possible to increase the effectiveness of UV filters in a perfuming solution. These oils in fact improve the solubility of the UV filters, so that it is possible to incorporate them in smaller amount while guaranteeing sufficient stabilization of the product. The inventors discovered that it is even possible to use only two UV filters for effectively stabilizing a perfuming solution exposed to UV.

SUMMARY OF THE INVENTION

The invention relates to a perfuming solution comprising at least one volatile alcohol, a perfume and a stabilizing mixture, said solution consisting of at least one UV filter selected from the derivatives of cinnamate, at least one UV filter selected from the derivatives of dibenzoylmethane, and at least one non-volatile oil that is soluble in said alcohol and is a solvent for said filters, the stabilizing mixture being in sufficient amount to protect the odour of the perfuming solution from degradation by UV radiation.

The combination of UV filters according to the invention has the advantage that it is less coloured than other known combinations of filters.

The invention also relates to the use, in a perfuming solution, of a combination of at least one UV filter selected from the derivatives of cinnamate, at least one UV filter selected from the derivatives of dibenzoylmethane and at least one non-volatile oil, as an agent for stabilizing the organoleptic properties, in particular the odour and optionally the colour, of said solution against UV radiation.

The invention also relates to a method for stabilizing the organoleptic properties, in particular the colour and/or the odour of a perfuming solution, characterized in that it consists of incorporating, in the solution, a combination of at least one UV filter selected from the derivatives of cinnamate, at least one UV filter selected from the derivatives of dibenzoylmethane and at least one non-volatile oil.

The invention further relates to a cosmetic method for perfuming keratinous materials, notably the skin, lips, hair, scalp, eyelashes, eyebrows or nails, comprising application of the perfuming solution as defined above on the keratinous materials.

DETAILED DESCRIPTION OF THE INVENTION

The invention relates firstly to a perfuming solution comprising at least one volatile alcohol, a perfume and a mixture for stabilizing said solution consisting of
- at least one UV filter selected from the derivatives of cinnamate,
- at least one UV filter selected from the derivatives of dibenzoylmethane, and
- at least one non-volatile oil that is soluble in said alcohol and is a solvent for said filters, the stabilizing mixture being in sufficient amount to protect the odour of the perfuming solution from degradation by UV radiation.

"Perfuming solution" means a composition containing an alcohol, preferably as the principal ingredient, in which a perfume is dissolved, leaving a perfume after application on keratinous materials. Water-in-oil and oil-in-water emulsions are excluded from this definition. The perfuming solution is advantageously translucent or transparent, which makes its protection against visible light and UV radiation even more necessary.

The perfuming solution according to the invention can be in the form of fresh water, toilet water, perfume water, after-shave lotion, make-up removing lotion, or care water.

The perfuming solution according to the present invention contains at least one volatile alcohol.

"Volatile alcohol" means, in the sense of the invention, any compound comprising at least one alcohol function notably having a vapour pressure, at 25° C. and 0.1 MPa, in the range from 0.13 to 40 000 Pa, preferably from 1.3 to 13 000 Pa, more preferably from 1.3 to 8000 Pa, for example above 2000 Pa.

The volatile alcohol according to the present invention is preferably selected from the monohydric alcohols having from 1 to 5 carbon atoms and in particular from methanol, ethanol, propanol, isopropanol, n-butanol, isobutanol, t-butanol, and mixtures thereof.

The volatile alcohol or alcohols are preferably present in amounts in the range from 40 to 95 wt. %, and more preferably in amounts in the range from 55 to 80 wt. % relative to the total weight of the solution.

According to a preferred embodiment, the solution contains water in an amount in the range from 0.01 to 20 wt. %, preferably from 0.1 to 15 wt. %, and more preferably from 0.2 to 12 wt. % relative to the total weight of the solution.

"Perfume" means an odorous substance or a mixture of odorous substances that evaporate at 25° C. Each perfume has what is called a top note, which is the odour that diffuses first on applying the perfume or on opening its container, a middle note which corresponds to the complete perfume (emission for some hours after the top note) and a basic note, which is the most persistent odour (emission for several hours after the middle note). The persistence of the basic note corresponds to the odour persistence of the perfume.

The perfume can for example be selected from compounds whose INCI name appearing in the list of ingredients of the perfuming solution offered for sale is "Perfume". A perfume is a compound that is at least partially volatile at room temperature, the odour of which is detected.

"Perfume" also means any organic compound that is able to perfume the skin, hair, scalp, lips or nails.

The amount of perfume, also called concentrate, will more preferably be from 3 to 50 wt. %, better still from 5 to 30 wt. %, even better 10 to 20 wt. % relative to the total weight of the solution.

Perfumes and aromas of natural or synthetic origin and mixtures thereof can be used as perfume in the perfuming solution of the invention. As perfumes and aromas of natural origin, we may mention for example extracts from flowers (lily, lavender, rose, jasmine, ylang-ylang), from stems and leaves (patchouli, geranium, petitgrain), from fruits (coriander, anise, cumin, juniper), from the rind of fruits (bergamot, lemon, orange), from roots (angelica, celery, cardamom, iris, sweet rush), from wood (pine wood, sandalwood, guaiacum, pink cedar), from herbs and grasses (tarragon, lemon grass, sage, thyme), from needles and branches (spruce, fir, pine, dwarf pine), from resins and balsams (galbanum, elemi, benzoin, myrrh, olibanum, opopanax).

As perfume of synthetic origin, we may mention for example benzyl acetate, benzyl benzoate, phenoxyethyl isobutyrate, p-tert-butylcyclohexyl acetate, citronellyl acetate, citronellyl formate, geranyl acetate, linalyl acetate, dimethylbenzylcarbinyl acetate, phenylethyl acetate, linalyl benzoate, benzyl formate, ethylmethylphenyl glycinate, alkylcyclohexyl propionate, styralyl propionate and benzyl salicylate, benzyl ethyl ether, linear alkanals having from 8 to 18 carbon atoms, citral, citronellal, citronellyloxyacetaldehyde, cyclamenaldehyde, hydroxycitronellal, lilial and bourgeonal, ionones such as alpha-isomethylionone, and methylcedryl ketone, anethole, citronellol, eugenol, isoeugenol, geraniol, linalol, phenylethyl alcohol, terpineol, terpenes. These compounds are often in the form of a mixture of two or more of these odorous substances.

Moreover, it is also possible to use essential oils, components of aromas, for example essences of sage, of chamomile, of clove, of lemon balm, of mint, of cinnamon tree leaves, of lime blossom, of juniper, of vetiver, of olibanum, of galbanum, of labolanum and of lavandin.

The following are preferably used as perfume, alone or mixed: essence of bergamot, dihydromyrcenol, lilial, lyral, citronellol, phenylethyl alcohol, alpha-hexylcinnamaldehyde, geraniol, benzylacetone, cyclamenaldehyde, linalol, ambroxane, indole, hedione, sandelice, essences of lemon, of mandarin and of orange, allylamine glycolate, cyclovertal, essence of lavandin, essence of sage, betadamascone, essence of geranium, cyclohexyl salicylate, phenylacetic acid, geranyl acetate, benzyl acetate, rose oxide.

Among the known olfactory notes, we may mention for example hesperide perfumes, aromatics, floral perfumes, musks, fruity perfumes, spicy perfumes, oriental perfumes, marine perfumes, aquatic notes, chypre perfumes, woody perfumes, ferns and mixtures thereof.

The perfume can also contain triethyl citrate as solvent and/or diluent.

The perfume generally represents from 5 to 40 wt. %, preferably from 10 to 30 wt. % of the weight of the perfuming solution of the invention.

The stabilizing mixture according to the invention comprises at least one UV filter selected from the derivatives of cinnamate and at least one UV filter selected from the derivatives of dibenzoylmethane. "UV filter" means any compound absorbing UV radiation in the wavelength range from 280 nm to 400 nm.

The perfuming solution is advantageously free from a UV filter selected from salicylate derivatives.

Among the UV filters derived from cinnamate, we may notably mention, non-exhaustively: ethyl-2-hexyl-p-methoxycinnamate, isopropyl-p-methoxycinnamate, isoamyl methoxycinnamate, cinoxate (2-ethoxyethyl-p-methoxycinnamate), diethanolamine methoxycinnamate, glyceryl ethyl-2-hexanoate di-p-methoxycinnamate, [4-bis(trimethylsiloxy)methylsilyl-3-methylbutyl]-3,4,5-trimethoxycinnamate.

Among the cinnamate derivatives mentioned above, ethyl-2-hexyl-p-methoxycinnamate, also called ethylhexyl methoxycinnamate or octyl methoxycinnamate, will be used quite particularly, and is offered for sale under the trade names PARSOL MCX from the company DSM NUTRITIONAL PRODUCTS, UVINUL MC 80 from the company BASF, and Uvinul A+B from the company BASF.

The UV filter selected from the derivatives of cinnamate represents from 20 to 90 wt. %, preferably from 30 to 75 wt. %, of the weight of the stabilizing mixture.

The UV filter selected from the derivatives of cinnamate advantageously represents from 0.3 to 0.4 wt. % of the weight of the perfuming solution.

Among the UV filters derived from dibenzoylmethane, we may notably mention, non-exhaustively: 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

Among the derivatives of dibenzoylmethane mentioned above, 4-(tert-butyl)-4'-methoxydibenzoylmethane, also called avobenzone or butylmethoxydibenzoylmethane (BM-DBM), will be used quite particularly, and is offered for sale under the trade names PARSOL 1789 of the company DSM NUTRITIONAL PRODUCTS, or EUSOLEX 9020 of the company MERCK.

The UV filter selected from the derivatives of dibenzoylmethane represents from 5 to 75 wt. %, preferably from 10 to 55 wt. %, of the weight of the stabilizing mixture.

The UV filter selected from the derivatives of dibenzoylmethane advantageously represents from 0.05 to 0.1 wt. % of the weight of the perfuming solution. The total amount of UV filters in the perfuming solution preferably represents from 0.005 to 5 wt. %, more preferably from 0.1 to 1 wt. %, of the weight of the perfuming solution.

The stabilizing mixture comprises, besides UV filters, at least one non-volatile oil.

"Oil" means, in the sense of the invention, a fat that is not soluble in water, and is liquid at 25° C. and 0.1 MPa. "Non-volatile oil" means any oil having a vapour pressure, at 25° C. and 0.1 MPa, that is not zero and is less than 2.6 Pa, preferably less than 0.13 Pa. In the sense of the present invention, a non-volatile oil is not a perfume and is not an organic UV filter.

According to a preferred embodiment, the non-volatile oil is different from any organic UV filter that has been previously described.

The non-volatile oil is preferably soluble at 25° C. in alcohol, which is usually the principal ingredient in terms of proportion by weight in the perfuming solution. The oil is preferably devoid of odour. The non-volatile oil is preferably colourless.

The non-volatile oil is preferably miscible with alcohol and is a solvent for said filters, preferably without supplying heat. The solubility of the non-volatile oil in the alcohol can be evaluated by the following protocol for measurement of miscibility. Weigh the alcohol selected (80 wt. %) in a beaker, then add the oil selected (20 wt. %) to the beaker. Stir for 5 minutes and then package the whole in a 120-ml pill box. Leave to stand for 24 hours at 25° C.

After standing for 24 hours, if the mixture is visually clear and homogeneous, it is considered that the oil is miscible with alcohol.

The oil is preferably polar, in the sense that it contains at least one, preferably at least two oxygen atoms or conjugated double bonds.

According to one embodiment, the oil is a hydrocarbon oil comprising at most one aliphatic ring. The oil is preferably an aliphatic oil, i.e. it is not aromatic in the sense that it does not contain a cyclic system obeying Hückel's aromaticity rule.

"Aliphatic" means a non-aromatic compound. "Aliphatic ester, ether, alcohol or acid" means a compound consisting of carbon atoms, hydrogen atoms and respectively a COO, COC, OH or COOH group. "Hydroxylated aliphatic ester" means a hydrocarbon compound comprising a COO group and at least one OH group, preferably a single OH group.

According to another embodiment, the oil is a silicone oil comprising at least one aromatic carbon-containing group.

"Aliphatic ester" means a compound consisting of carbon atoms, hydrogen atoms and at least one COO group. "Monoester" means a compound comprising a COO group, and "diester" means a compound comprising two COO groups.

"Hydroxylated ester" means a compound comprising at least one COO group and at least one OH group.

In another embodiment, an ester selected from aliphatic monoesters and diesters is preferred. The hydroxylated esters are preferably non-aromatic.

The non-volatile oil is preferably selected from aliphatic mono- and diesters, non-hydroxylated aromatic esters, aliphatic carbonates and phenylated silicones.

As polar oils usable in the perfuming solution of the invention, we may mention for example:
 aliphatic mono- and diesters, notably i) monoesters of a linear or branched, saturated or unsaturated, preferably saturated, aliphatic carboxylic acid comprising 8 to 20 carbon atoms, and of an aliphatic monohydric alcohol comprising 3 to 20 carbon atoms, ii) aliphatic diesters of an aliphatic dicarboxylic acid comprising 4 to 10 carbon atoms and of a monohydric alcohol,
 monoesters of benzoic acid and of an aliphatic alcohol comprising 8 to 20 carbon atoms, ethyl-2-hexyl benzoate, octyl-2-dodecyl benzoate, isostearyl benzoate, $C_{12}$-$C_{15}$ alkylbenzoate,
 dialkyl carbonates whose alkyl groups contain from 8 to 18 carbon atoms such as dicaprylyl carbonate, di(ethyl-2-hexyl)carbonate, hydroxylated aliphatic mono- or diesters such as i) esters of a hydroxylated aliphatic mono- or dicarboxylic acid comprising 3 to 20 carbon atoms, and of an aliphatic monohydric alcohol comprising 6 to 20 carbon atoms, for example isostearyl lactate, octyl hydroxystearate, octyldodecyl hydroxystearate, cetyl lactate, myristyl lactate, diisostearyl malate, or ii) aliphatic mono- and diesters of polyols, in particular of diols and of triols, such as esters of an aliphatic monocarboxylic acid comprising 3 to 20 carbon atoms, and of an aliphatic diol or triol comprising 3 to 20 carbon atoms, saturated or unsaturated aliphatic alcohols having from 8 to 26 carbon atoms, such as octyldodecanol, octyldecanol, 2-butyloctanol, 2-hexyldecanol, 2-undecylpentadecanol, saturated or unsaturated aliphatic monocarboxylic acids having from 7 to 29 carbon atoms such as oleic acid, linoleic acid, linolenic acid or isostearic acid, silicone oils having at least one alkoxy or phenyl group, pendant or at the end of the silicone chain, having from 2 to 24 carbon atoms, notably phenyltrimethicone, phenyldimethicones, phenyltrimethylsiloxydiphenylsiloxanes, diphenyldimethicones, diphenylmethyldiphenyl-trisiloxanes, 2-phenylethyl trimethylsiloxysilicates, and polymethylphenylsiloxanes;

mixtures thereof.

Among the aliphatic mono- and diesters, esters comprising from 10 to 25 carbon atoms, preferably from 14 to 22 carbon atoms, are preferred, for example esters of isononanoic acid such as isononyl isononanoate, isodecyl isononanoate, decyl-2-hexyl isononanoate, isostearyl isononanoate, cetearyl isononanoate, tridecyl isononanoate.

We may also mention isopropyl myristate, ethyl-2-hexyl palmitate, octyl-2-dodecyl stearate, octyl-2-dodecyl erucate, isostearyl isostearate, octyl dodecyl stearoyl stearate, isostearyl palmitate, isocetyl stearate, octyldodecyl myristate, triisostearyl trilinoleate, octyldodecyl neodecanoate, octyldodecyl octanoate, isobutyl stearate, isodecyl neopentanoate, octyldodecyl neopentanoate, ethyl-2-hexyl isostearate, butyl isostearate, isopropyl palmitate, stearyl heptanoate, isopropyl stearate, isostearyl neopentanoate, isopropyl isostearate, cetyl octanoate (or palmityl octanoate), butyl stearate, hexyl laurate (or hexyl dodecanoate), ethyl laurate, decyl oleate, oleyl oleate, myristyl myristate, hexyldecyl dimethyloctanoate, isocetyl isostearate, hexyl-2-decyl myristate, heptyl-2-undecyl palmitate, cetyl-2-ethylhexanoate.

Among the esters of dicarboxylic acids, we may also mention diethyl-2-hexyl)sebacate, diisopropyl sebacate, diethyl-2-hexyl)succinate, di(hexyl-2-decyl)adipate, di(heptyl-2-undecyl)adipate.

Among the polyol mono- and diesters, we may mention the diesters of alkylene glycol with an aliphatic acid having from 6 to 20 carbon atoms, such as propylene glycol dioctanoate, neopentyl glycol diheptanoate and diethylene glycol diisononanoate; butylene glycol dicaprate/dicaprylate, propylene glycol dicaprate/dicaprylate, neopentyl glycol dicaprate, diethylene glycol diisononanoate, propylene glycol diisostearate, propylene glycol dipelargonate, propylene glycol dioctanoate, neopentyl glycol diheptanoate, tripropylene glycol dipivalate; and glyceryl monoalkanoates such as glyceryl heptanoate, glyceryl octanoate, and glyceryl decanoate.

According to one embodiment of the invention, the non-volatile oil is a non-volatile aliphatic ester comprising from 10 to 25 carbon atoms, preferably from to 22 carbon atoms. The aliphatic ester can be selected from non-hydroxylated esters of aliphatic $C_2$ to $C_{18}$ monocarboxylic or dicarboxylic acids and of alcohols selected from $C_2$ to $C_{20}$ monohydric alcohols and $C_2$ to $C_8$ polyols.

The non-volatile oil preferably represents from 1 to 30 wt. %, more preferably from 10 to 20 wt. % of the weight of the stabilizing mixture, notably about 15 wt. % of the stabilizing mixture.

The non-volatile oil preferably represents from 0.001 to 1 wt. %, preferably from 0.05 to 0.5 wt. % of the perfuming solution.

According to one embodiment, the stabilizing mixture preferably comprises at most two UV filters. A preferred stabilizing mixture consists of octyl methoxycinnamate, butylmethoxydibenzoylmethane and a non-volatile oil selected from the group comprising diisostearyl malate, phenyltrimethicone, butylene glycol dicaprylate/dicaprate, $C_{12}$-$C_{15}$ alkyl benzoate and isononyl isononanoate.

A more preferred stabilizing mixture consists of octyl methoxycinnamate, butyl methoxy-dibenzoylmethane and butylene glycol dicaprylate/dicaprate. The octyl methoxycinnamate represents advantageously from 60 to 80% by weight of the stabilizing mixture. The butyl methoxy-dibenzoylmethane represents advantageously from 10 to 20% by weight of the stabilizing mixture, and the butylene glycol dicaprylate/dicaprate represents advantageously from 10 to 20% by weight of the stabilizing mixture.

The stabilizing mixture represents from 0.01 to 10 wt. %, preferably from 0.1 to 5 wt. %, more preferably from 0.05 to 3 wt. % and even more preferably from 0.1 to 2 wt. %, of the weight of the perfuming solution.

The solution according to the invention can further comprise at least one dye such as fat-soluble dyes, water-soluble dyes or dyes soluble in an aqueous-alcoholic solution.

The combination of UV filters according to the invention also plays a role of protection with respect to these dyes, in order to avoid any colour change connected either directly with the reaction of light or of temperature on these dyes or the interaction of the perfumes or derivatives thereof resulting from degradation on said dyes.

The water-soluble dyes or those soluble in an aqueous-alcoholic solution are for example: caramel, Yellow 5, Acid Blue 9/Blue 1, Green 5, Green 3/Fast Green FCF 3, Orange 4, Red 4/Food Red 1, Yellow 6, Acid Red 33/Food Red 12, Red 40, cochineal carmine (CI 15850, CI 75470), Ext. Violet 2, Red 6-7, Ferric Ferrocyanide, Ultramarines, Acid Yellow 3/Yellow 10, Acid Blue 3, Yellow 10. The fat-soluble dyes are for example Sudan Red, D&C Red 17, D&C Green 6, beta-carotene, soya oil, Sudan Brown, D&C Yellow 11, D&C Violet 2, D&C Orange 5, quinoline yellow, annatto.

The dyes generally represent from 0.01 to 1 wt. %, preferably from 0.05 to 0.5 wt. % of the weight of the perfuming solution.

The perfuming solution of the invention can further comprise any additive usually employed in the area of perfumes, notably selected from the antioxidants. Among the antioxidants, we may mention for example ascorbic acid, di-tert-butyl-p-hydroxytoluene (also called BHT or 2,6-di-tert-butyl-p-cresol), BHA (tert-butyl-4-hydroxyanisole), tocopherols such as vitamin E, derivatives of tocopherol such as tocopheryl acetate, gallic acid and derivatives thereof.

The solution according to the invention can be manufactured by the known methods generally used in the field of perfumed compositions.

The perfuming solutions according to the invention can be packaged in the form of bottles. They can also be applied in the form of fine droplets by means of pressurized devices. The devices according to the invention are well known by a person skilled in the art and comprise non-aerosol pumps or "atomizers", aerosol containers comprising a propellant as well as aerosol pumps using compressed air as propellant.

The aerosol-packaged solutions according to the invention generally contain conventional propellants such as for example hydrofluorinated compounds, dichlorodifluoromethane, difluoroethane, dimethyl ether, isobutane, n-butane, propane, trichlorofluoromethane.

The perfuming solutions according to the invention are notably in the form of aqueous-alcoholic solutions.

The present invention further relates to the use of a stabilizing mixture as described above and comprising at least one UV filter derived from cinnamate, at least one UV filter derived from dibenzoylmethane, and at least one oil selected from butylene glycol dicaprylate/dicaprate, phenyltrimethicone, diisostearyl malate, isononyl isononanoate and dicapryl carbonate for protecting a perfuming solution from degradation of its odour by UV radiation.

The perfuming solution can further contain at least one dye, in which case the stabilizing mixture protects the perfuming solution from degradation of its colour by UV radiation.

The stabilizing mixture preferably represents from 0.01 to 10 wt. %, preferably from 0.1 to 5 wt. % of the weight of the perfuming solution.

The characteristics described in relation to the perfuming solution are applicable to the use of a stabilizing mixture according to the invention.

Other aims, features and advantages of the invention will become clear to a person skilled in the art on reading the examples, which are given purely for illustration and therefore will not limit the scope of the invention in any way. The examples form an integral part of the present invention and are thus of general application.

Moreover, in the following examples, all percentages are given by weight, temperature is expressed in degrees Celsius unless stated otherwise, and pressure is atmospheric pressure.

EXAMPLES

A—Preparation of the Perfuming Solutions

Perfuming solutions, also called fragrances, were prepared with the following composition:

TABLE 1

|  | Fragrance No. 1 | Fragrance No. 2 | Fragrance No. 3 |
|---|---|---|---|
| Alcohol at 96.2 vol. % | Q.s. 100 | Q.s. 100 | Q.s. 100 |
| Concentrate | 11.00 of concentrate No. 1 | 17.85 of concentrate No. 2 | 30.00 of concentrate No. 3 |
| Purified water | 10.38 | 2.54 | 0.56 |
| dyes | 0.11 | 0.10 | 0.43 |
| BHT | $5 \times 10^{-3}$ | $5 \times 10^{-3}$ | $1 \times 10^{-2}$ |

Concentrate No. 1 was mainly composed of hedione, concentrate No. 2 was mainly composed of rose essence, and concentrate No. 3 was mainly composed of jasmine absolute. In each of these fragrances, a mixture of filters and of non-volatile oil according to the invention was incorporated having one of the following four compositions:

TABLE 2

|  | Mixture 1 | Mixture 2 | Mixture 3 | Mixture 4 |
|---|---|---|---|---|
|  | 70% OCTYL METHOXYCINNAMATE 15% BMDBM* | | | |
| DIISOSTEARYL MALATE | 15% | | | |
| PHENYL TRIMETHICONE | | 15% | | |
| BUTYLENE GLYCOL DICAPRYLATE/ DICAPRATE | | | 15% | |
| ISONONYL ISONONANOATE | | | | 15% |

*BMDBM: 4-(tert-butyl)-4'-methoxydibenzoylmethane

The ethanol and the water were mixed cold in a beaker with Ystral stirring for 5 min. The dyes were then added, in the form of a solution in ethanol or in water as appropriate, to the aqueous-alcoholic mixture, and stirred for 5 minutes.

The antioxidant BHT, BMDBM, octyl methoxycinnamate and the non-volatile oil were mixed in a dish at 70° C. with magnetic stirring, varying the amount of the mixture in the fragrance between 0.1 and 5 wt. %.

Then the mixture was left to cool and the perfume was added, with magnetic stirring.

The contents of the dish were then mixed with the coloured aqueous-alcoholic solution with stirring for 10 min, packaged in a perfume atomizer for testing sprayability, in 30-ml pill boxes filled to 25 ml for stove stabilities, then in 60-ml glass bottles for the SUN TEST and olfactory testing.

B—Stability and Sensory Assessment of the Perfuming Solutions

We then evaluated the thermal stability, cold stability and stability to UV radiation of each of the three fragrances, to which one of the four mixtures described above was added, according to the following protocols.

Stability of Homogeneity of the Solution in a Stove at 4° C. and 45° C.

The 30-ml pill boxes, filled to 25 ml with a fragrance, are put in a stove at 45° C. and in a refrigerator at 4° C. for 3 months. The solution is stable (compliant result) if there is no phase separation or clouding or significant deposit.

Stability of the Colour and of the Odour to UV

The L*a*b* colour coordinates of the mixture, placed in a 60-ml glass bottle filled to 55 ml with a fragrance, were measured before irradiation by means of a Minolta 3600D CM, POS 0118 spectro-colorimeter.

The bottles, each containing one fragrance, are placed upright, which permits complete exposure of the bottle to UV, for 12 hours in the following conditions.

Each sample is irradiated in a Suntest™ apparatus, model CPS. The UV source used is a xenon lamp emitting between 300 and 800 nm at a power of 765 W/m². The xenon lamp is associated with a "short cut-off" quartz filter combined with "UV Special Glass". The sample is maintained at a temperature of 25° C. (using cooling and/or air conditioning plates).

After 12 hours of irradiation, the L*a*b* coordinates of the perfuming solution were measured again. The colour of the solution is considered stable (compliant result) if the difference between the two measurements in standard conditions of measurement ($D_{65}$ illuminant and Observer at 10°), expressed by delta E, is less than 5, preferably less than 1.

The odour of the perfuming solution before and after exposure to UV radiation in the conditions described above is also evaluated by an olfactory expert.

The test result is deemed compliant if the olfactory expert does not detect any significant difference in intensity of odour after exposure to UV radiation.

Greasy Sensation Left on the Skin (Sensory Assessment)

The fragrance was applied on the neck by spraying with an atomizer, and the aim was to detect any residual greasy sensation left on the skin, once the alcohol and water had evaporated.

Assessment is based on residual greasy sensation on the skin, or on visual observations (residual greasy film or clothing stained).

For example, a solution containing fragrance No. 2 and 10 wt. % of mixture 2, 3 or 4 is judged too greasy by the expert.

The test result is deemed compliant if the expert does not detect an uncomfortable sensation and there is no observation of greasiness.

The results of these various assessments are reported in Tables 3 to 8 below. The statements in parentheses qualify the result obtained without altering its compliance. The statements in italics characterize observations that make the result non-compliant.

TABLE 3

| Fragrance No. 2 + X % of the mixture | | Mixture 1 | Mixture 2 | Mixture 3 | Mixture 4 |
|---|---|---|---|---|---|
| 0.1 | STOVE STABILITY 4° C. | Compliant | Compliant | Compliant | Compliant |
| | 45° C. | Compliant | Compliant | Compliant | Compliant |
| | SUN TEST 12 H | Compliant | Compliant | Compliant | Compliant |
| | SENSORY ASSESSMENT | Compliant | Compliant | Compliant | Compliant |
| | OLFACTORY TEST AFTER 12 H OF SUN TEST | Olfactory note compliant | Olfactory note compliant | Olfactory note compliant | Olfactory note compliant |
| 0.5 | STOVE STABILITY 4° C. | Compliant | Compliant | Compliant | Compliant |
| | 45° C. | Compliant | Compliant | Compliant | Compliant |
| | SUN TEST 12 H | Compliant | Compliant | Compliant | Compliant |
| | SENSORY ASSESSMENT | Compliant | Compliant | Compliant | Compliant |
| | OLFACTORY TEST AFTER 12 H OF SUN TEST | Olfactory note compliant | Olfactory note compliant | Olfactory note compliant | Olfactory note compliant |
| 1 | STOVE STABILITY 4° C. | Compliant | Compliant | Compliant | Compliant |
| | 45° C. | Compliant | Compliant | Compliant | Compliant |
| | SUN TEST 12 H | Compliant | Compliant | Compliant | Compliant |
| | SENSORY ASSESSMENT | Compliant | Compliant | Compliant | Compliant |
| | OLFACTORY TEST AFTER 12 H OF SUN TEST | Olfactory note compliant | Olfactory note compliant | Olfactory note compliant | Olfactory note compliant |
| 5 | STOVE STABILITY 4° C. | Compliant | Compliant | Compliant | Compliant |
| | 45° C. | Compliant | Compliant | Compliant | Compliant |
| | SUN TEST 12 H | Compliant | Compliant | Compliant | Compliant |
| | SENSORY ASSESSMENT | Compliant (slightly greasy) | Compliant (slightly greasy) | Compliant (slightly greasy) | Compliant (slightly greasy) |
| | OLFACTORY TEST AFTER 12 H OF SUN TEST | Olfactory note compliant (slight loss of intensity). | Olfactory note compliant (slight loss of intensity). | Olfactory note compliant (slight loss of intensity). | Olfactory note compliant (slight loss of intensity). |

TABLE 4

| | | Fragrance No. 1 | Fragrance No. 1 + 0.5% Mixture 1 | Fragrance No. 1 + 0.5% Mixture 2 | Fragrance No. 1 + 0.5% Mixture 3 | Fragrance No. 1 + 0.5% Mixture 4 |
|---|---|---|---|---|---|---|
| STOVE STABILITIES | 45° C. | Compliant | Compliant | Compliant | Compliant | Compliant |
| | 4° C. | Compliant | Compliant | Compliant | Compliant | Compliant |
| SUN TEST 12 H | | complete decoloration | Compliant (slightly pinkish) | Compliant (slightly pinkish) | Compliant (slightly pinkish) | Compliant (slightly pinkish) |
| SENSORY ASSESSMENT | | — | Compliant (no greasy effect on the skin) | Compliant (no greasy effect on the skin) | Compliant (no greasy effect on the skin) | Compliant (no greasy effect on the skin) |
| OLFACTORY TEST AFTER 12 H OF SUN TEST | | Loss of intensity of olfactory note | Olfactory note compliant | Olfactory note compliant | Olfactory note compliant | Olfactory note compliant |

TABLE 5

|  | | Fragrance No. 3 | Fragrance No. 3 + 1% Mixture 1 | Fragrance No. 3 + 1% Mixture 2 | Fragrance No. 3 + 1% Mixture 3 | Fragrance No. 3 + 1% Mixture 4 |
|---|---|---|---|---|---|---|
| STOVE | 45° C. | Compliant | Compliant | Compliant | Compliant | Compliant |
| STABILITIES | 4° C. | Compliant (very slight wisps) | Compliant | Compliant | Compliant | Compliant |
| SUN TEST 12 H | | complete decoloration | Compliant (slightly decoloured) | Compliant (slightly decoloured) | Compliant (slightly decoloured) | Compliant (slightly decoloured) |
| SENSORY ASSESSMENT | | — | Compliant (no greasy effect on the skin) | Compliant (no greasy effect on the skin) | Compliant (no greasy effect on the skin) | Compliant (no greasy effect on the skin) |
| OLFACTORY TEST AFTER 12 H OF SUN TEST | | Loss of intensity of olfactory note | Olfactory note compliant | Olfactory note compliant | Olfactory note compliant | Olfactory note compliant |

TABLE 6

|  | | Fragrance No. 1 + 5% Additive 1 | Fragrance No. 1 + 5% Additive 2 | Fragrance No. 1 + 5% Additive 3 | Fragrance No. 1 + 5% Additive 4 |
|---|---|---|---|---|---|
| STOVE | 45° C. | Compliant | Compliant | Compliant | Compliant |
| STABILITIES | 4° C. | Compliant | Compliant | Compliant | Compliant |
| SUN TEST 12 H | | Compliant (slight yellowing) | Compliant (slight yellowing) | Compliant (slight yellowing) | Compliant (slight yellowing) |
| SENSORY ASSESSMENT | | Compliant (slightly greasy) | Compliant (slightly greasy) | compliant (slightly greasy) | Compliant (slightly greasy) |
| OLFACTORY AFTER 12 H OF SUN TEST | | Olfactory note compliant (slight loss of intensity). | Olfactory note compliant (slight loss of intensity). | Olfactory note compliant (slight loss of intensity). | Olfactory note compliant (slight loss of intensity). |

TABLE 7

| | Fragrance No. 2 + 0.5% of the mixture of the invention | | | |
|---|---|---|---|---|
| | Comparative Test 1 | Test 2 | Test 3 | Test 4 |
| | Composition of the mixture | | | |
| OCTYL METHOXYCINNAMATE | 82.3 | 70 | 50 | 35 |
| BMDBM | 17.7 | 15 | 35 | 50 |
| BUTYLENE GLYCOL DICAPRYLATE/DICAPRATE | 0 | 15 | 15 | 15 |
| STOVE 45° C. | Compliant | Compliant | Compliant | Compliant |
| STABILITIES 4° C. | Compliant | Compliant | Compliant | Compliant |
| SUN TEST 12 H | Decoloration | Compliant | Compliant | Compliant |
| SENSORY ASSESSMENT | Compliant | Compliant | Compliant | Compliant |
| OLFACTORY AFTER 12 H OF SUN TEST | Loss of intensity of the olfactory note | Compliant | Compliant | Compliant |

TABLE 8

|  | | Fragrance No. 2 only | Fragrance No. 2 + 0.5% Comparative test 1 | Fragrance No. 2 + 0.5% Mixture 2 | Fragrance No. 2 + 0.5% Mixture 3 | Fragrance No. 2 + 0.5% Mixture 4 |
|---|---|---|---|---|---|---|
| STOVE | 45° C. | Compliant | Compliant | Compliant | Compliant | Compliant |
| STABILITIES | 4° C. | White deposit | Compliant | Compliant | Compliant | Compliant |
| SUN TEST 12 H | | complete decoloration | decoloration | Compliant (slightly decoloured) | Compliant (slightly decoloured) | Compliant (slightly decoloured) |
| SENSORY ASSESSMENT | | — | Compliant | Compliant (no greasy effect on the skin) | Compliant (no greasy effect on the skin) | Compliant (no greasy effect on the skin) |
| OLFACTORY TEST AFTER 12 H OF SUN TEST | | Loss of intensity of olfactory note | Loss of intensity of olfactory note | Compliant | Compliant | Compliant |

*cf. composition of the mixture "Comparative test 1" in Table 7.

The invention claimed is:

1. Perfuming solution comprising at least one volatile alcohol, a perfume and a mixture for stabilizing said solution, the stabilizing mixture consisting of
   at least one first UV filter selected from derivatives of cinnamate,
   at least one second UV filter selected from derivatives of dibenzoylmethane, and
   at least one non-volatile oil selected from the group consisting of aliphatic mono- and diesters, non-hydroxylated aromatic esters, aliphatic carbonates and phenylated silicones, the stabilizing mixture being in a sufficient amount to protect the odor of the perfuming solution from degradation by UV radiation,
   wherein the perfuming solution comprises no UV filters other than the first and second UV filters in the stabilizing mixture,
   wherein the volatile alcohol or alcohols are present in amounts in the range from 40 to 95 wt. % relative to the total weight of the solution,
   wherein the UV filter selected from the derivatives of cinnamate represents from 20 to 90 wt. % of the weight of the stabilizing mixture,
   wherein the UV filter selected from the derivatives of dibenzoylmethane represents from 5 to 75 wt. % of the weight of the stabilizing mixture, and
   wherein the non-volatile oil represents from 10 to 20 wt. % of the weight of the stabilizing mixture.

2. Perfuming solution according to claim 1, wherein the volatile alcohol is selected from the monohydric alcohols having from 1 to 5 carbon atoms and in particular from methanol, ethanol, propanol, isopropanol, n-butanol, isobutanol, t-butanol, and mixtures thereof.

3. Perfuming solution according to claim 1, wherein the volatile alcohol or alcohols are present in amounts in the range from 55 to 80 wt. % relative to the total weight of the solution.

4. Perfuming solution according to claim 1, wherein the UV filter selected from the derivatives of cinnamate is ethyl-2-hexyl-p-methoxycinnamate, isopropyl-p-methoxycinnamate, isoamyl methoxycinnamate, cinoxate (2-ethoxyethyl-p-methoxycinnamate), diethanolamine methoxycinnamate, glyceryl ethyl-2-hexanoate di-p-methoxycinnamate or [4-bis(trimethylsiloxy)methylsilyl-3-methylbutyl]-3,4,5-trimethoxycinnamate.

5. Perfuming solution according to claim 1, wherein the UV filter selected from the derivatives of cinnamate represents from 30 to 75 wt. %, of the weight of the stabilizing mixture.

6. Perfuming solution according to claim 1, wherein the UV filter selected from the derivatives of cinnamate represents from 0.3 to 0.4 wt. % of the weight of the perfuming solution.

7. Perfuming solution according to claim 1, wherein the UV filter selected from the derivatives of dibenzoylmethane is 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane or 2,6-dimethyl-4-tert-butyl-4'-methoxydibenzoylmethane.

8. Perfuming solution according to claim 1, wherein the UV filter selected from the derivatives of dibenzoylmethane represents from 10 to 55 wt. %, of the weight of the stabilizing mixture.

9. Perfuming solution according to claim 1, wherein the UV filter selected from the derivatives of dibenzoylmethane represents from 0.05 to 0.1 wt. % of the weight of the perfuming solution.

10. Perfuming solution according to claim 1, wherein the non-volatile oil is selected from a group consisting of isononyl isononanoate, butylene glycol dicaprylate/dicaprate, phenyltrimethicone, diisostearyl malate, $C_{12}$-$C_{15}$ alkyl-benzoate, and dicapryl carbonate.

11. Perfuming solution according to claim 1, wherein the non-volatile oil represents from 0.001 to 1 wt. % of the perfuming solution.

12. Perfuming solution according to claim 1, wherein the stabilizing mixture represents from 0.01 to 10 wt. % of the weight of the perfuming solution.

13. Perfuming solution according to claim 1, wherein the total amount of UV filters in the perfuming solution represents from 0.005 to 5 wt. % of the weight of the perfuming solution.

14. Method for protecting a perfuming solution from degradation of its odor by UV radiation, comprising adding to the solution a sufficient amount of a stabilizing mixture consisting of at least one UV filter derived from cinnamate, at least one UV filter derived from dibenzoylmethane, and at least one oil selected from the group consisting of butylene glycol dicaprylate/dicaprate, phenyltrimethicone, diisostearyl malate, isononyl isononanoate and dicapryl carbonate, to form the perfuming solution according to claim 1.

* * * * *